Figure 2:
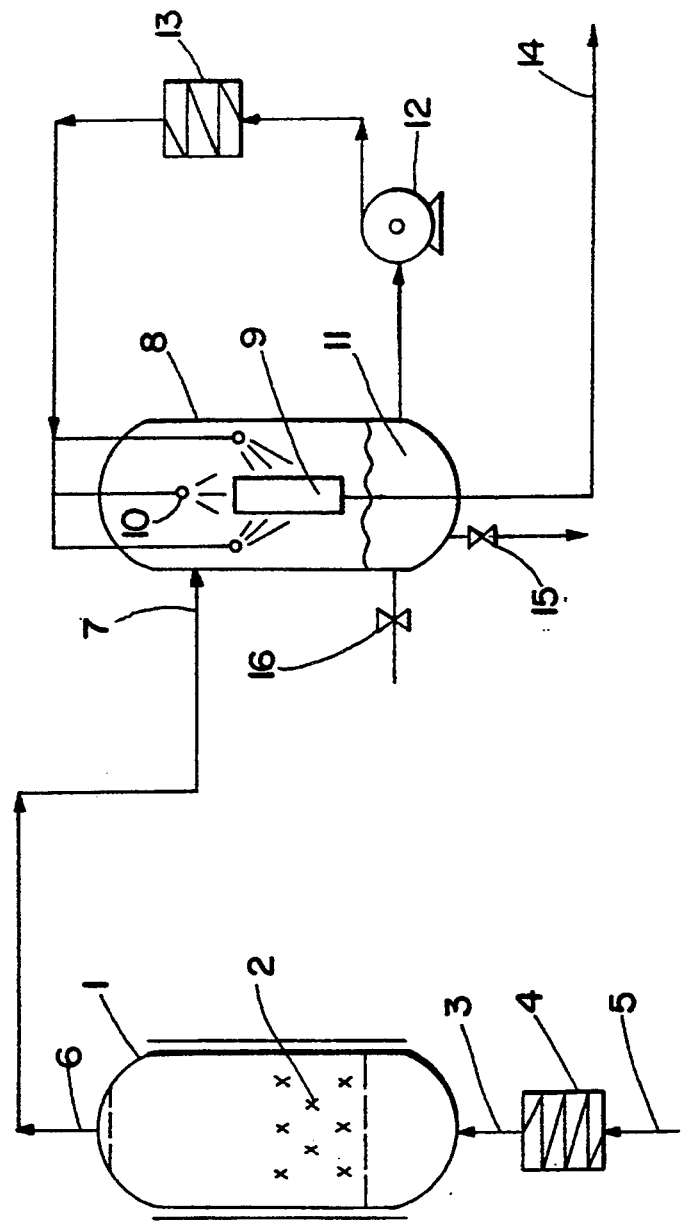

United States Patent [19]

Sipos et al.

[11] Patent Number: 5,399,688
[45] Date of Patent: Mar. 21, 1995

[54] CAFFEINE RECOVERY FROM ACTIVATED CARBON

[75] Inventors: Stefan Sipos, Bremen, Germany; Gabriel von Lengyel-Konopi, Thundorf, Switzerland

[73] Assignee: Jacobs Suchard AG, Zurich, Switzerland

[21] Appl. No.: 92,340

[22] Filed: Jul. 15, 1993

[30] Foreign Application Priority Data

Aug. 18, 1992 [EP] European Pat. Off. .............. 9114065

[51] Int. Cl.6 .......................................... C07D 473/12
[52] U.S. Cl. .................................... 544/275; 544/274
[58] Field of Search .............................. 544/275, 276

[56] References Cited

U.S. PATENT DOCUMENTS 4,673,743 6/1987 Wilkins ............................. 544/275
4,877,631 10/1989 Kaper et al. ....................... 426/422

Primary Examiner—Nicholas Rizzo
Attorney, Agent, or Firm—Thomas A. Marcoux; Thomas R. Savoie

[57] ABSTRACT

The invention relates to a process for recovering caffeine from caffeine-loaded activated carbon and which is characterized in that the caffeine destroying activity of the activated carbon is reduced before or after loading with caffeine. The activated carbon can to that end be treated with acids, buffers, complexing agents, redox substances, caffeine and other xanthine derivatives. The caffeine recovery yield can be considerably increased by this means.

10 Claims, 1 Drawing Sheet

CAFFEINE RECOVERY FROM ACTIVATED CARBON

The present invention relates to an improved process for recovery of caffeine from caffeine-loaded activated carbon.

With a number of decaffeination processes for vegetable products, including coffee, activated carbon is used at some stage for selective separation of the caffeine. Because the caffeine obtained as a by-product can be used for other purposes, efforts are made to separate the caffeine from the activated carbon by economical means.

The desorption of the caffeine from the activated carbon is not easy because activated carbon is a very good adsorbent for caffeine. U.S. Pat. No. 4,673,743 to Wilkens describes a process for separating caffeine from caffeine-loaded activated carbon with which a circulated inert gas sweeping stream is passed rectangularly through the activated carbon at a temperature of 350° to 450° C., and the caffeine desorbed from the activated carbon is precipitated by cooling in the form of solid particles and separated. One essential disadvantage of that process is the fact that the activated carbon layer thickness or bed depth cannot be more than 60 mm. If the layer thickness is increased, the caffeine yield decreases considerably.

A further disadvantage of that process resides in that a considerable part of the caffeine cannot be recovered but is lost.

U.S. patent application Ser. No. 08/092,339 (filed Jul. 15, 1993); describes a process for recovery of caffeine from activated carbon which permits the successful use of significantly deeper beds for desorption and which reduces the process time and the quantity of hot gas or steam required per unit of carbon desorbed, thereby making the entire process economically attractive. That process uses a circulated inert gas sweeping stream held at a temperature of 250° to 460° C. and is characterized in that the activated carbon is preheated prior to the desorption of the caffeine with external heating means and held during the desorption step at a uniform temperature or at a temperature increasing from the inlet to the outlet of the inert gas sweeping stream within the range of 250° to 460° C. and the caffeine is subsequently separated from the inert gas sweeping stream by conventional means. The preheating preferably takes place at a temperature of at least 250° C., especially at least 320° C.

It is possible with that process to eliminate a substantial disadvantage of the process of the above-mentioned U.S. Pat. No. 4,673,743. It is, however, also disadvantageous with that process that a part of the caffeine is irretrievably lost.

It is therefore the object of the present invention to find a process with which it is possible to reduce to a minimum the caffeine losses resulting upon recovery of caffeine from caffeine-loaded activated carbon.

It has been found within the scope of the present invention that the losses with the recovery of caffeine from caffeine-loaded activated carbon are to be attributed to an apparent caffeine destroying activity of activated carbon. Consequently, the invention relates to a process for recovering caffeine from caffeine-loaded activated carbon and which is characterized in that the caffeine destroying activity of activated carbon is reduced before or after loading with caffeine.

It has been established within the scope of the invention that the caffeine destroying activity of activated carbon can be reduced by various means. The activated carbon can be treated according to the invention with acids, buffers, complexing agents, redox substances, caffeine and other xanthine derivatives. In all cases, a considerable reduction in the extent of the decomposition of the caffeine is achieved during the recovery and the yield of caffeine there with considerably increases.

the drawings show in

Figure 1:
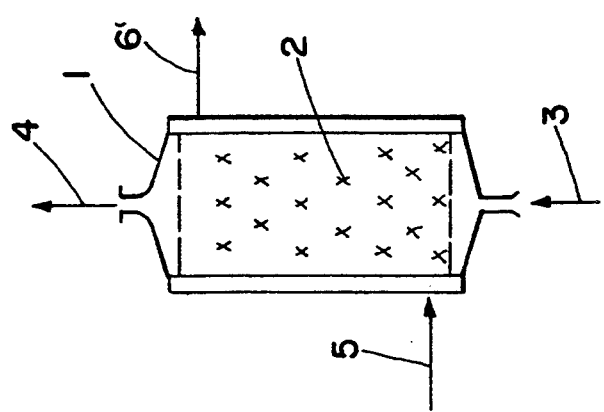

FIG. 1 the schematic representation of an apparatus for the treatment of the activated carbon according to the invention, and FIG. 2 a schematic representation of an apparatus for the recovery of caffein from activated carbon as used in the examples.

The invention works by treating the activated carbon, either before or after loading it with caffeine, prior to thermal caffeine recovery processes, in order to reduce the caffeine destroying activity of the activated carbon.

The treatment of the activated carbon with the agent for reducing the caffein destroying activity can be carried out, for instance, in an apparatus as it is shown in FIG. 1. The meanings of the numerals in FIG. 1 are 1 a jacketed activated carbon treatment column, 2 the activated carbon to be treated, 3 the inlet for the treatment solution and 4 the outlet for the treatment solution. 5 and 6 are the inlet and outlet for a heating medium optionally to be used.

As already mentioned above, the most varied treatment agents have proven to be useful. That gives rise to the assumption that the caffeine destroying activity of activated carbon is to be attributed to various causes. Acids, buffers, complexing agents, redox substances and also the additional loading with caffeine or other xanthine derivatives have proven to be useful.

Inorganic and/or organic acids come under consideration as suitable acids for carrying out the process of the invention. For instance, phosphoric acid, sulfuric acid, nitric acid, hydrochloric acid, acetic acid, citric acid, gluconic acid, formic acid, perchloric acid, phytic acid, lactic acid, ascorbic acid, isoascorbic acid, etc., are suitable.

The strength of the acids used as well as their amounts vary depending both on the type of activated carbon to be treated as well as the contacting apparatus used. Acid concentration will generally vary between 0.001N to 10N and more, preferably be between 0.01 and 5N. Usage ratios will be 0.5 to 30 1/1 of carbon and more, preferably between 1 and 10.

The increase in the caffeine yield with the recovery from caffeine-loaded activated carbon by means of the treatment according to the invention with acid is surprising because other tests in respect of the recovery of caffeine had shown that pure caffeine readily sublimes, on the other hand, crude caffeine from coffee decaffeination decomposes but can readily be brought to sublimation when it is made alkaline with CaO or MgO.

A possible explanation for the mode of operation of the acids could possibly be seen in that the metal content of the carbon has a causal influence on the decomposition of the caffeine and the treatment according to the invention with acid leads to a reduction in the metal content of the activated carbon.

For instance, practically the most diverse buffers which regulate pH in the acid range (as, for example, HCl/KCl, citric acid/NaCl, citric acid/NaOH, acetic acid/Na acetate, etc.) and especially those on the basis of the aforementioned acids and their salts, especially some of their combinations with ammonia (as, for example, citric acid/NH$_4$OH, acetic acid/NH$_4$OH, etc.), can be quoted as buffers suitable according to the invention. Strengths and amounts correspond to those used for acids. Solutions based on metaphosphates, pyrophosphates, polyphosphates and other phosphates are also suitable.

The sodium salt of ethylenediaminetetraacetic acid (EDTANa$_2$), phytates, gluconic acid, and practically all the numerous well-known heavy and transition metal complexing agents, under also well-known suitable conditions, are to be quoted as complexing agents suitable according to the invention.

Suitable redox compounds are, for example, nitric acid, perchloric acid, ascorbic acid, isoascorbic acid, etc. Strengths and amounts of complexing agents and redox compounds correspond to the ones to be used for the acids.

Combinations of acids and/or buffers and/or complexing agents and/or redox compounds can also be used within the scope of the invention.

Even caffeine itself showed a positive effect on recovery yields. A more fully loaded carbon shows not only a definitive yield improvement in percent but also an absolute lower caffeine loss. The same effect was able to be achieved by "uploading" the carbon before subjecting it to the recovery process. Xanthine derivatives other than caffeine can also be used successfully.

The carbon coming from the decaffeination process as a rule has a degreee of caffeine loading of 15 to 19% by weight (dry basis). In accordance with the invention, the carbon 20% should be loaded to the extent that the loading is at least 20% by weight, preferably at least 24% by weight, caffeine and optionally other xanthine derivatives Uploading the activated carbon with caffeine and other xanthine derivatives can be effected in very diverse forms. One of the preferred ways is to reload the used activated carbon into the adsorber section of the decaffeination plant in such a way that it is in contact with the caffeine rich stream just prior to its separation from caffeine with fresh carbon. Another possibility for effecting the uploading is to contact it with a partial caffeine solution recycle just prior to the recovery unit or with a xanthine derivative solution. This, of course, has the disadvantage of increase in the content of water which has to be dried off in the immediately following step, but avoids the need for a larger (for example, high-pressure) adsorbing unit in the decaffeination plant.

Xanthine derivatives which can be used here are compounds with chemical, structural and behavioral similarity to caffeine. Examples are isocaffeine, all dimethylxanthines (theobromine, theophylline, paraxanthine), diverse monomethylxanthines, etc., all very similar in their chemical structure, adsorption behavior with respect to activated carbon, sublimability, etc.

In a preferred embodiment of the invention, the activated carbon is treated with acids, buffers, complexing agents and/or redox compounds and additionally—either fully high level loaded or uploaded—with caffeine or other xanthine derivatives.

As already mentioned, the treatment according to the invention can be carried out in a simple batch vessel as shown in FIG. 1, stirrer or pumping devices optionally being used to improve intimate contact between the treatment agents and the activated carbon.

The treatment duration can be from a few to several hours and preferably from 10 minutes to 3 hours. The treatment normally takes place at room temperature but can also be at elevated temperatures, for instance in the range from 40° to 180° C., preferably in the range from 60° to 110° C.

After the treatment according to the invention, the activated carbon can optionally be washed with water in order to remove excess treatment agents (acid, buffer, etc.).

In the case of treatment with HCl, there should at any event be washing with water. It has proven necessary that chloride ions be removed as far as possible. Washing is preferably at elevated temperatures of, for example, 80° to 100° C. The disturbing chloride ions can, however, also be removed by displacement with other ions, e.g. NO$_3$— or OH—. A thermal treatment in an oven at about 500° to 700° C. can also be used for this purpose.

The treatment of the activated carbon according to the invention can take place before or after loading it with caffeine within the scope of the decaffeination process. The caffeine adsorbing properties (loading levels and kinetics) are not negatively influenced by a treatment beforehand. To the contrary, unusually high caffeine recovery yields are possible with the process of the invention. The process thereby has the additional advantage that the activated carbon can be used again immediately after the recovery of the caffeine without need of a reactivation of the activated carbon.

EXAMPLE

The treatment according to the invention was carried out with an apparatus as shown in FIG. 1. 500 g of activated carbon were washed with 3250 ml of 0.1N agents (H$_3$PO$_4$, HCl, EDTANa$_2$) in a one-way through fashion at a flow rate of 2.5 l/hr followed by removing excess agents by a 2 hr hot (80° C.) water wash.

The activated carbon treated by this means was then introduced into an apparatus as it is shown in FIG. 2. That apparatus works according to the process which is described in U.S. patent application Ser. No. 08/092,339 (filed Jul. 15, 1993). and is similar to the apparatus described there but has a fluidized bed (with externally heated walls). With that process, the activated carbon loaded with caffeine and treated according to the invention is, as already mentioned above, rapidly brought to a uniform temperature suitable for the desorption of the caffeine from the activated carbon with the aid of an external heating and a hot inert gas sweeping stream before desorption of the caffeine is commenced.

The individual reference numerals in FIG. 2 have the following meanings:

1. activated carbon desorption vessel with electrically heated walls, an internal diameter of 100 mm, perforated plates for producing a fluidized bed and with a total height of about 900 mm.
2. fluidized carbon bed (static bed heights 100 to 120 mm)
3. inert gas sweeping stream (N$_2$), 380° C., 9 st m$_3$/hr
4. gas heater
5. gas source
6. caffeine-loaded inert gas sweeping stream, 380° C., exiting from 1

7. caffeine-loaded inert gas sweeping stream, 380° C., entering the caffeine collection vessel 8
8. caffeine collection vessel
9. 20 μ sintered metal filter
10. caffeine solution wash sprays (aqueous, 60° C.)
11. caffeine solution
12. recirculation pump
13. heat exchanger
14. exiting inert gas sweeping stream freed of caffeine
15. caffeine solution drain
16. make-up water.

The desorption vessel 1 was in each experiment first filled with 500 g of material and rapidly brought to a temperature of 380° C. with the aid of external heating and the inert gas sweeping stream. The flow rate of the inert gas sweeping stream ($N_2$) was 9 st m3/hr, and its temperature was 380° C. The residence time was 3 hrs in all cases. All carbon samples had been loaded with caffeine in an industrial supercritical $CO_2$ decaffeination plant, except the $EDTANa_2$ one which was loaded in a respective pilot plant.

The results of the experiments are set forth in the following Tables 1 to 4. The treatment process according to the invention, the caffeine loading of the activated carbon at the beginning of the experiments and the recovery yield are quoted. Absolute loss values are additionally contained in Table 2.

The results of experiments with activated carbon treated according to the invention ($H_3PO_4$, HCl) and untreated activated carbon are compared in Table 1. The recovery yield values show that considerable increases are possible with the process of the invention.

The result of an experiment is given in Table 2 with which the caffeine loading of the activated carbon had been purposively increased, and it is shown that substantially higher recovery yields, namely about twice as high, are possible in comparison with normally loaded activated carbon.

Experiments are described in Table 3 with which two measures according to the invention have been combined, namely, on the one hand, the treatment with acid or, resp., complexing agent and, on the other hand, a purposive additional caffeine loading, with yields of more than twice as high, reaching to almost 100%, being possible.

It is shown in Table 4 that the activated carbon treated according to the process of the invention has reattained its original adsorbing properties after recovery of the caffeine so that a reactivation of the activated carbons prior to their renewed use is not necessary. The caffeine adsorbing activity was measured according to a test where a certain amount of activated carbon adsorbs pure caffeine from a standard aqueous solution, two different caffeine/carbon contact times (2 and 16 hours) being used to represent both the kinetics of adsorption influence and the maximum absolute loading capacity of the material. The test is run at 25° C. and the results are expressed as percentage caffeine on dry caffeine + carbon basis. From the two values, it is possible to infer the behavior of the activated carbon under super-critical $CO_2$ decaffeination conditions, as experience shows.

TABLE 1

Effects of carbon pretreatment on recovery yield

| Experiment No. | Carbon Quality | Caffeine load on carbon at start, % dry basis | Recovery yield |
|---|---|---|---|
| 1 | untreated | 15.2 | 43% |
| 2 | $H_3PO_4/H_2O$ | 14.6 | 67% |
| 3 | $HCl/H_2O$/temp.*) | 14.3 | 74% |

*)temp. means a treatment of the HCl treated carbon in an oven at a temperature between 500° and 700° C.

TABLE 2

Effects of caffeine levels (uploading) on recovery yields, also illustrating absolute caffeine losses.

| Exper. No. | Carbon Quality | Caffeine load on carbon at start, % dry basis | Recovery yield | Absolute loss |
|---|---|---|---|---|
| 1 | untreated | 15.2 | 43% | 38 g from 80 g |
| 4 | untreated | 21.8 | 82% | 17 g from 96 g |

TABLE 3

Effects of both treatments and caffeine levels (uploading) on recovery yields

| Experiment No. | Carbon Quality | Caffeine load on carbon at start, % dry basis | Recovery yield |
|---|---|---|---|
| 1 | untreated | 15.2 | 43% |
| 5 | $H_3PO_4/H_2O$ | 24.1 | 99% |
| 6 | $HCl/H_2O$/temp. | 23.3 | 94% |
| 7 | $EDTANa_2/H_2O$ | 21.0 | 97% |

TABLE 4

Caffeine adsorbing properties of activated carbon after caffeine loading in an industrial supercritical $CO_2$ decaffeination plant and subsequent thermal desorption/sublimation with inert gas sweeping stream

| Experiment No. | Carbon Quality | Caffeine adsorbing activity | |
|---|---|---|---|
| | | in 2 hrs | in 16 hrs |
|  | typical untreated fresh | 20–22 | 28–29 |
|  | typical treated fresh | 20–22 | 28–29 |
| 1 | untreated | 19.7 | 28.2 |
| 5 | $H_3PO_4/H_2O$ | 21.2 | 29.4 |
| 6 | $HCl/H_2O$/temp. | 20.8 | 28.6 |

We claim:

1. A process for recovering caffeine from caffeine-loaded activated carbon wherein the caffeine destroying activity of the activated carbon is reduced by treating the activated carbon with acids, buffers, complexing agents, redox substances, caffeine or xanthine derivatives other than caffeine at a solution concentration of about 0.001 to 10N, a temperature of 20° to 180° C. and a time period of 10 minutes to 3 hours, and then recovering the caffeine by thermal desorption/sublimation at temperatures between 250° and 460° C. using an inert gas sweeping stream.

2. The process of claim 1 wherein the solution concentration is at about 0.01 to 5N, solutions.

3. The process of claim 1 wherein the acid is $H_3PO_4$, $H_2SO_4$, $HNO_3$, HCl, acetic acid, gluconic acid, formic acid, perchloric acid, phytic acid, lactic acid, ascorbic, isoascorbic acid, citric acid, or combinations thereof.

4. The process of claim 1 wherein the buffer is HCl/KCl, citric acid/NaCl, citric acid/$NH_4OH$, citric acid/NaOH, acetic acid/Na acetate, or acetic acid/$NH_4OH$.

5. The process of claim 1 wherein the complexing agent is $EDTANa_2$, phytate, or gluconic acid.

6. The process of claim 1 wherein the redox substance is nitric acid, perchloric acid, ascorbic acid or isoascorbic acid.

7. The process of claim 1 wherein combinations of acids and/or buffers and/or complexing agents and/or redox compounds are used.

8. The process of claim 1 wherein the activated carbon is loaded up to a concentration of at least 20% by weight of caffeine, isocaffeine, dimethylxanthines or methylxanthines (based on the weight of dry carbon), before the recovery of the caffeine.

9. The process of claim 8 wherein the additional loading is up to a concentration of at least 24%.

10. The process of claim 1 wherein the treatment of the activated carbon is at 60° to 110° C.

* * * * *